Figure 1:
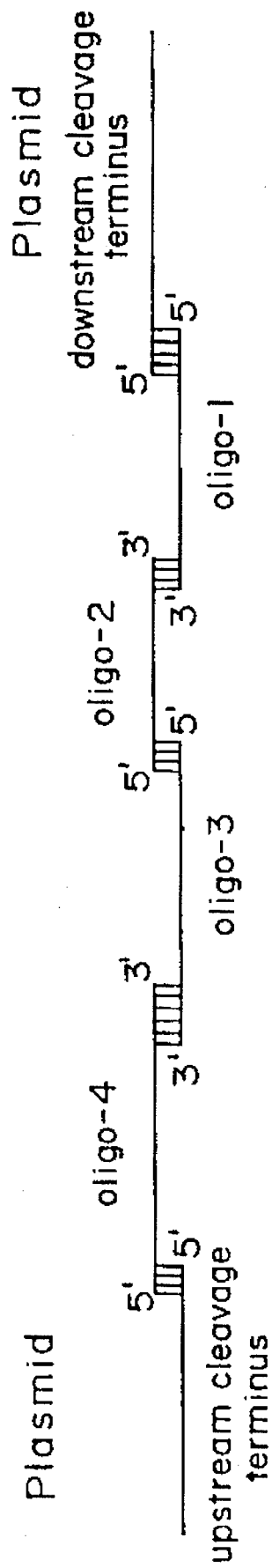
Figure 6:
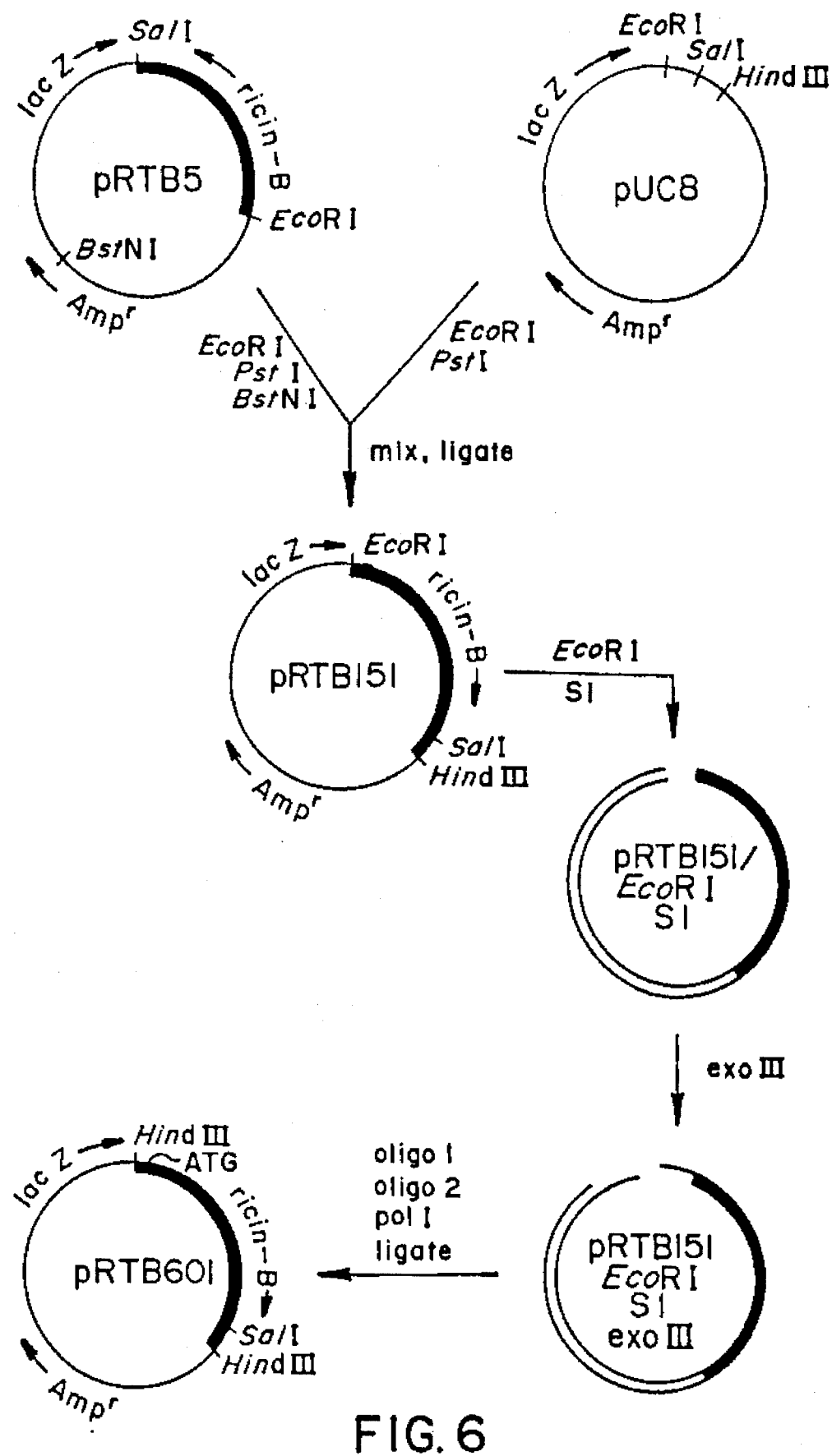
Figure 7:
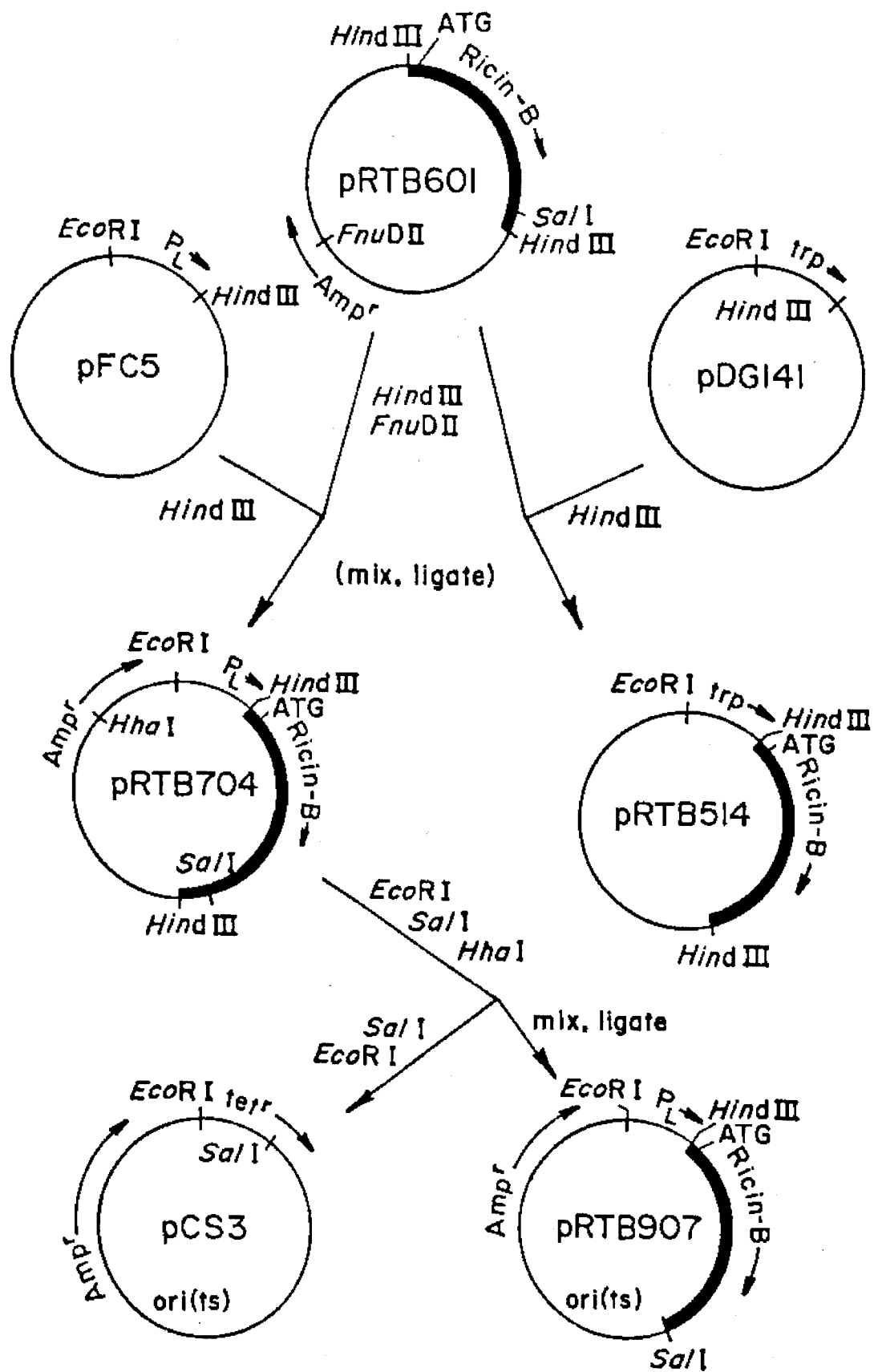

US005538868A

United States Patent [19]

Horn et al.

[11] Patent Number: 5,538,868
[45] Date of Patent: Jul. 23, 1996

[54] RECOMBINANT RICIN TOXIN FRAGMENTS

[75] Inventors: Glenn T. Horn, Emeryville; Michael Piatak, Jr., Walnut Creek, both of Calif.

[73] Assignee: Cetus Oncology Corporation, Emeryville, Calif.

[21] Appl. No.: 376,286

[22] Filed: Jan. 23, 1995

Related U.S. Application Data

[63] Continuation of Ser. No. 717,319, Mar. 29, 1985, abandoned, which is a continuation-in-part of Ser. No. 578,121, Feb. 8, 1984, abandoned.

[51] Int. Cl.$^6$ .......................... C12P 19/34; C12N 15/09; C12N 15/63
[52] U.S. Cl. .................. 435/91.1; 435/69.1; 435/71.2; 435/71.3; 935/11; 935/27; 935/29; 935/38; 935/56; 935/73
[58] Field of Search ................................ 435/69.1, 70.1, 435/71.1, 71.2, 71.3, 90, 172.3, 91.1; 935/27, 44, 11, 29, 28, 37, 38, 34, 50, 56, 73, 69

[56] References Cited

U.S. PATENT DOCUMENTS 4,740,461  4/1988  Kaufman .................. 435/69.1

FOREIGN PATENT DOCUMENTS

| 0145111 | 6/1985 | European Pat. Off. |
| 8319265 | 7/1983 | United Kingdom. |
| 8406569 | 3/1984 | United Kingdom. |

OTHER PUBLICATIONS

Bolivar et al., "Construction and Characterization of New Cloning Vehicles," *Gene*, 2:95–113 (1977).
Butterworth and Lord, "Ricin and *Ricinus communis* agglutinin subunits are all derived from a single-size polypeptide precursor," *Eur J. Biochem*, 137:57–65 (1983).
Cawley et al., "Homology Between Ricin and *Ricinus communis* Agglutinin: Amino Terminal Sequence Analysis and Protein Synthesis Inhibition Studies," *Arch Biochem Biophys*, 190(2):744–755 (Oct., 1978).
Clewell et al., "Nature of Col E$_1$ Plasmid Replication in *Escherichia coli* in the Presence of Chloramphenicol," *J. Bacteriol.* 110(2):667–676 (May, 1972).
Clewell et al., "Supercoiled Circular DNA–Protein Complex in *Escherichia Coli*: Purification and Induced Conversion to an Open Circular DNA Form," *Proc. Natl. Acad. Sci.*, 62:1159–1166 (1969).
Cohen et al., "Nonchromosomal Antibiotic Resistance in Bacteria: Genetic Transformation of *Escherichia coli* by R–Factor DNa,"*Proc. Natl. Acad. Sci.* (USA), 69(8):2110–2114 (Aug., 1972).
Erlich et al.,, "Identification of an Antigen–Specific Immunogobulin M Antibody Asociated with Acute *Toxoplasma* Infection," *Infect. Immun.*, 41:683–690 (Aug., 1983).
Fiers et al., "Complete nucleotide sequence of SV40 DNA", *Nature*, 273:113–120 (May 11, 1978).
Funatsu et al., "Separation of the Two Constituent Polypeptide Chains of Ricin D," *Agric. Biol. Chem.*, 41(7):1211–1215 (1977).
Gelfand et al., "Isolation and characterization of a ColE1–derived plasmid copy–number mutant," *Proc. Natl. Acad. Sci.* (USA), 75(12):5869–5873 (Dec., 1978).

(List continued on next page.)

*Primary Examiner*—Mindy Fleisher
*Assistant Examiner*—Nancy J. Degen
*Attorney, Agent, or Firm*—Philip L. McGarrigle; Li-Hsien Rin-Laures; Robert P. Blackburn

[57] ABSTRACT

Recombinant vectors and methods for constructing ricin B are disclosed. The coding sequence for ricin B was cloned, disposed in suitable expression vectors and produced free of components normally accompanying this peptide. In addition, a novel means of reconstructing missing portions of coding sequence, and certain improvements in messenger RNA purification are disclosed.

10 Claims, 9 Drawing Sheets

OTHER PUBLICATIONS

Goeddel et al, "Synthesis of human fibroblast interferon by *E. coli*," *Nucl. Acids Res.*, 8(18):4057–4074 (1980).

Graham et al., "A New Technique for the Assay of Infectivity of Human Adenovirus 5 DNA", *Virology*, 52:456–467 (1973).

Grunstein and Hogness, "Colony hybridization: A method for the isolation of cloned DNAs that contain a specific gene," *Proc. Natl. Acad. Sci* (USA), 72(10):3961–3965 (Oct., 1975).

Hess et al., "Cooperation of Glycolytic Enzymes," *J. Adv. Enzyme Reg.*, 7:149–167 (1968).

Holland and Holland, "Isolation and Identification of Yeast Messenger Ribonucleic Acids Coding for Enolase, Glyceraldehye-3-phosphate Dehydrogenase, and Phosphoglycerate Kinase", *Biochemistry*, 17:4900–4907 (1978).

Matteucci and Caruthers, "Synthesis of Deoxyoligonucleotides on a Polymer Support," *J. Am. Chem. Soc.*, 103:3185–3191 (1981).

Maxam and Gilbert, "Sequencing End–Labeled DNA with Base–Specific Chemical Cleavages", *Meth. Enzymol.*, 65:499–560 (1980).

Meselon and Yuan, "DNA Restriction Enzyme from *E. Coli*," *Nature*, 217:1110–1114 (Mar. 23, 1968).

Messing et al., "A system for shotgun DNA sequencing", *Nucl. Acids Res.*, 9(2):309–321 (1981).

O'Farrell et al., "Regulated Expression by Readthrough Translation from a Plasmid–Encoded β–Galactosidase," *J. Bacteriology*, 134(2):645–654 (May, 1978).

Shimatake and Rosenberg, "Purified λ regulatory protein cII positively activates promoters for lysogenic development," *Nature*, 292:128–132 (Jul. 9, 1981).

Stinchcomb et al., "Isolation and characterization of a yeast chromosomal replicator", *Nature*, 282:39–43 (Nov., 1979).

Talmadge and Gilbert, "Construction of plasmid vectors with unique cloning sites in signal sequence coding region," *Gene*, 12:235–241 (1980).

Tschumper and Carbon, "Sequence of a yeast DNA fragment containing a chromosomal replicator and the TRP1 gene," *Gene*, 10:157–166 (1980).

Wong, "Temperature–sensitive copy number mutants of ColE1 are located in an untranslated region of the plasmid genome," *Proc. Natl. Acad. Sci.* (USA), 79:3570–3574 (Jun., 1982).

Funatsu et al. (1979) Agricultural & Biological Chemistry, vol. 43, pp. 2221.

Olsnes et al. (1982) in *Molecular Action of Toxins and Viruses*, Elsevier Press, N.Y. pp. 51–103.

Suggs et al. (1981) *PNAS* vol. 78 pp. 6613–6617.

Jaye et al. (1983) *Nucleic Acids Res.* vol. 11 pp. 2325–2335.

Goeddel et al. (1980) *Nature* vol. 281 pp. 412–416.

FIG. 2

Ricin-B Protein Sequence

AlaAspValCysMetAspProGluProIleValArgIleValGlyArgAsnGlyLeuCys

ValAsnValArgAspGlyArgPheAsnHisGlyAsnAlaIleGlnLeuTrpProCysLys

SerAsnThrAspAlaAsnGlnLeuThrLeuLysArgAspAsnThrIleArgSerAsnGly

LysCysLeuThrThrTyrGlyTyrProSerGlyValTyrValMetIleTyrAspCysAsn

ThrAlaAlaThrThrAlaAspArgGluIleTrpAsnAsnGlyThrIleIleAsnProArg

SerSerLeuValLeuAlaAlaThrSerGlyAsnSerGlyThrThrLeuThrValGlnThr

AsnIleTyrAlaValSerGlnGlyProLeuPheThrAsnAsnThrGlnProTrpValThr

ThrIleValGlyLeuTyrGlyLeuCysLeuGlnAlaAsnSerGlyGlnValValIleGlu

AspSerCysSerGluLysAlaGluGlnGlnTrpAlaLeuTyrAlaSerGlyAsnIleAsn

ProGlnGlnArgArgAspAsnCysLeuThrSerAspSerAsnIleArgGluThrValVal

LysIleLeuSerCysGlyProAlaSerSerGlyGluArg<u>TrpMetPheLysAsnAspGly</u>

ThrIleLeuAsnLeuTyrSerGlyLeuValLeuAspValArgAlaSerAspProSerLeu

LysGlnIleIleLeuTyrProLeuTrpGlyHisAspProAsnGlnLeuIleLeuProPhe (260 a.a -- from Funatsu)

FIG. 3
Comparison of Ricin-B Sequence with RTB-5

R-AlaAspValCysMetAspProGluProIleValArgIleValGlyArgAsnGlyLeuCys
　　　　　　　　　　　　　　　　　　　ArgIleValGlyArgAsnGlyLeuCys
　　　　　　　　　　　　　　　　gaattccGCGTATCGTAGGTCGAAATGGTCTATGT R-ValAsnValArgAspGlyArgPheAsnHisGlyAsnAlaIleGlnLeuTrpProCysLys
　ValAspValArgAspGlyArgPheHisAsnGlyAsnAlaIleGlnLeuTrpProCysLys
　GTTGATGTTAGGGATGGAAGATTCCACAACGGAAACGCAATACAGTTGTGGCCATGCAAG R-SerAsnThrAspAlaAsnGlnLeu　　　ThrLeuLysArgAspAsnThrIleArgSerAsn
　SerAsnThrAspAlaAsnGlnLeuTrpThrLeuLysArgAspAsnThrIleArgSerAsn
　TCTAATACAGATGCAAATCAGCTCTGGACTTTGAAAAGAGACAATACTATTCGATCTAAT R-GlyLysCysLeuThrThrTyrGlyTyrProSerGlyValTyrValMetIleTyrAspCys
　GlyLysCysLeuThrThrTyrGlyTyrSerProGlyValTyrValMetIleTyrAspCys
　GGAAAGTGTTTAACTACTTACGGGTACAGTCCGGGAGTCTATGTGATGATCTATGATTGC R-AsnThrAlaAlaThrThrAlaAspArg　　GluIleTrpAsnAsnGlyThrIleIleAsnPro
　AsnThrAlaAlaThrAspAlaThrArgTrpGlnIleTrpAspAsnGlyThrIleIleAsnPro
　AATACTGCTGCAACTGATGCCACCCGCTGGCAAATATGGGATAATGGAACCATCATAAATCCC R-ArgSerSerLeuValLeuAlaAlaThrSerGlyAsnSerGlyThrThrLeuThrValGlnThr
　ArgSerGlyLeuValLeuAlaAlaThrSerGlyAsnSerGlyThrThrLeuThrValGlnThr
　AGATCTAGTCTAGTTTTAGCAGCGACATCAGGCAACAGTGGTACCACACTTACAGTGCAAACC R-AsnIleTyrAlaValSerGlnGlyProLeuPheThrAsnAsnThrGlnProTrpValThr
　AsnIleTyrAlaValSerGlnGlyTrpLeuProThrAsnAsnThrGlnProPheValThr
　AACATTTATGCCGTTAGTCAAGGTTGGCTTCCTACTAATAATACACAACCTTTTGTGACA R-ThrIleValGlyLeuTyrGlyLeuCysLeuGlnAlaAsnSerGlyGlnValValIleGlu
　ThrIleValGlyLeuTyrGlyLeuCysLeuGlnAlaAsnSerGlyGlnValTrpIleGlu
　ACCATTGTTGGGCTATACGGTCTGTGCTTGCAAGCAAATAGTGGACAAGTATGGATAGAG R-AspSerCysSerGluLysAlaGluGlnGlnTrpAlaLeuTyrAlaSerGlyAsnIleAsn
　AspCysSerSerGluLysAlaGluGlnGlnTrpAlaLeuTyrAlaAspGlySerIleArg
　GACTGTAGCAGTGAAAAGGCTGAACAACAGTGGGCTCTTTATGCAGATGGTTCAATACGT R-ProGlnGlnArgArgAspAsnCysLeuThrSerAspSerAsnIleArgGluThrValVal
　ProGlnGlnAsnArgAspAsnCysLeuThrSerAspSerAsnIleArgGluThrValVal
　CCTCAGCAAAACCGAGATAATTGCCTTACAAGTGATTCTAATATACGGGAAACAGTTGTC R-LysIleLeuSerCysGlyProAlaSerSerGlyGluArgTrpMetPheLysAsnAspGly
　LysIleLeuSerCysGlyProAlaSerSerGlyGlnArgTrpMetPheLysAsnAspGly
　AAGATCCTCTCTTGTGGCCCTGCATCCTCTGGCCAACGATGGATGTTCAAGAATGATGGA R-ThrIleLeuAsnLeuTyrSerGlyLeuValLeuAspValArgAlaSerAspProSerLeu
　ThrIleLeuAsnLeuTyrSerGlyLeuValLeuAspValArgAlaSerAspProSerLeu
　ACCATTTTAAATTTGTATAGTGGGTTGGTGTTAGATGTGAGGGCATCGGATCCGAGCCTT R-LysGlnIleIleLeuTyrProLeuTrpGlyHisAspProAsnGlnLeu　　IleLeuProPhe
　LysGlnIleIleLeuTyrProLeu　　HisGlyAspProAsnGlnIleTrpLeuProLeuPheTerTer
　AAACAAATCATTCTTTACCCTCTC　　CATGGTGACCCAAACCAAATATGGTTACCATTATTTTGATAG ACAGATTACTCTCTTGCAGTGTGTATGTCCTGCCATGAAAATAGATGGCTTAAATAAAAA
　GGACATTGTAAATTTTGTAACTGAAAGGACAGCAAGTTATTGCAGTCCAGTATCTAATAA
　GAGCACAACTATTGTCTTGTGCAAAAAA....

FIG. 4a

Sequences of pRTA-115, pRTB-4 and pRTB-5 Cloned Inserts

115-TATTAATCCCTATCATAGCTCTCATGGTGTATAGATGCGCACCTCCACCGTCGTCACAGTT

115-TTCTTTGCTTATAAGGCCAGTGGTGCCAAATTTTAATGCTGATGTTTGTATGGATCCTGAGC

RTA-115 <-(EcoRI)-> RTB-4
115-CCATAGTGCGTATCGTAGGTCGAAATGGTCTATGTGTTGATGTTACAGGTGAAGAATTCTAC
 5-gaattccGCGTATCGTAGGTCGAAATGGTCTATGTGTTGATGTTAGGGATGGAAGATTCCAC 4-GATGGAAACCCAATACAATTGTGGCCTTGCAAATCTAATACAGACTGGAATCAGTTATGGA
 5-AACGGAAACGCAATACAGTTGTGGCCATGCAAGTCTAATACAGATGCAAATCAGCTCTGGA 4-CTTTGAGAAAAGACGGTACAATTCGATCTAATGGCAAGTGTTTGACCATTTATAAGTCCAG
 5-CTTTGAAAAGAGACAATACTATTCGATCTAATGGAAAGTGTTAACTACTTACGGGTACAG 4-TCTAGGAAAGCATGTGATGATATATAATTGTACTACCGCTACAGTTGGTGCCACCCGTTGG
 5-TCCGGGAGTCTATGTGATGATCTATGATTGCAATACTGCTGCAACTGATGCCACCCGCTGG 4-CAAATATGGGACAACCGAACCATCATAAATCCCATATCTGGTTTAGTTTTGGCAGCCACAT
 5-CAAATATGGGATAATGGAACCATCATAAATCCCAGATCTAGTCTAGTTTTAGCAGCGACAT 4-CAGGAAACAGTGGTACCACACTTACAGTGCAAACCAACATTTATGCCGTTAGTCAAGGTTG
 5-CAGGCAACAGTGGTACCACACTTACAGTGCAAACCAACATTTATGCCGTTAGTCAAGGTTG 4-GCTTCCTAGTAATAATACACAACCTTTTGTGACATCCATTGTTGGGCTAAATGATCTCTGT
 5-GCTTCCTACTAATAATACACAACCTTTTGTGACAACCATTGTTGGGCTATACGGTCTGTGC 4-TTACAAGCAAATACTGGAAAAGTATGGTTAGACGAGTGTACAAGTGAAAAGGCTGAACAAC
 5-TTGCAAGCAAATAGTGGACAAGTATGGATAGAGGACTGTAGCAGTGAAAAGGCTGAACAAC 4-AATGGGCGCTTTATGCAGATGGTTCAATACGGCCTCAGCAAAACCAAGATAACTGCCTTAC
 5-AGTGGGCTCTTTATGCAGATGGTTCAATACGTCCTCAGCAAAACCGAGATAATTGCCTTAC 4-AAGTGATGCTAATATACGAGAAACAATTGTCAAGACCCTCTCTTGCAGCACTGCATCCTCC
 5-AAGTGATTCTAATATACGGGAAACAGTTGTCAAGATCCTCTCTTGTGGCCCTGCATCCTCT 4-GGCCAGCGATGGATGTTCAAGAATGATGGAACCATTTGGAATTTGTATAATGGATTGGTGT
 5-GGCCAACGATGGATGTTCAAGAATGATGGAACCATTTTAAATTTGTATAGTGGGTTGGTGT 4-TAGATGTGAAGCGATCGGATCCGACCCTTAAACAAATCATTATTTACCCTTTCCATGGAAA
 5-TAGATGTGAGGGCATCGGATCCGAGCCTTAAACAAATCATTCTTTACCCTCTCCATGGTGA 4-CCCAAACCAAATATGGTTTCCACTATTTTGATAGACTAATTACCCTCTTGCAGTGTATGTA
 5-CCCAAACCAAATATGGTTACCATTATTTTGATAGACAGATTACTCTCTTGCAGTGTGTATG 4-TGTCCTACCATGAACATAGTTG CTTAAATAAAAAGGACATTGTAAATTAAAAAAA...
 5- TCCTGCCATGAAAATAGATGGCTTAAATAAAAAGGACATTGTAAATTTTGTAACTGAAA

5-GGACAGCAAGTTATTGCAGTCCAGTATCTAATAAGAGCACAACTATTGTCTTGTGCAAAAAA...

FIG. 4b
Comparison of Translated Protein of RTB4 to RTB5

```
RTB-4: GAATTCTACGATGGAAACCCAATACAATTGTGGCCTTGCAAATCTAATACAGACTGGAAT
RTB-4: GluPheTyrAspGlyAsnProIleGlnLeuTrpProCysLysSerAsnThrAspTrpAsn
RTB-5: ArgPheHisAsnGlyAsnAlaIleGlnLeuTrpProCysLysSerAsnThrAspAlaAsn

CAGTTATGGACTTTGAGAAAAGACGGTACAATTCGATCTAATGGCAAGTGTTTGACCATT
4-GlnLeuTrpThrLeuArgLysAspGlyThrIleArgSerAsnGlyLysCysLeuThrIle
5-GlnLeuTrpThrLeuLysArgAspAsnThrIleArgSerAsnGlyLysCysLeuThrThr

TATAAGTCCAGTCTAGGAAAGCATGTGATGATATATAATTGTACTACCGCTACAGTTGGT
4-TyrLysSerSerLeuGlyLysHisValMetIleTyrAsnCysThrThrAlaThrValGly
5-TyrGlyTyrSerProGlyValTyrValMetIleTyrAspCysAsnThrAlaAlaThrAsp

GCCACCCGTTGGCAAATATGGGACAACCGAACCATCATAAATCCCATATCTGGTTTAGTT
4-AlaThrArgTrpGlnIleTrpAspAsnArgThrIleIleAsnProIleSerGlyLeuVal
5-AlaThrArgTrpGlnIleTrpAspAsnGlyThrIleIleAsnProArgSerGlyLeuVal

TTGGCAGCCACATCAGGAAACAGTGGTACCACACTTACAGTGCAAACCAACATTTATGCC
4-LeuAlaAlaThrSerGlyAsnSerGlyThrThrLeuThrValGlnThrAsnIleTyrAla
5-LeuAlaAlaThrSerGlyAsnSerGlyThrThrLeuThrValGlnThrAsnIleTyrAla

GTTAGTCAAGGTTGGCTTCCTAGTAATAATACACAACCTTTTGTGACATCCATTGTTGGG
4-ValSerGlnGlyTrpLeuProSerAsnAsnThrGlnProPheValThrSerIleValGly
5-ValSerGlnGlyTrpLeuProThrAsnAsnThrGlnProPheValThrThrIleValGly

CTAAATGATCTCTGTTTACAAGCAAATACTGGAAAAGTATGGTTAGACGAGTGTACAAGT
4-LeuAsnAspLeuCysLeuGlnAlaAsnThrGlyLysValTrpLeuAspGluCysThrSer
5-LeuTyrGlyLeuCysLeuGlnAlaAsnSerGlyGlnValTrpIleGluAspCysSerSer

GAAAAGGCTGAACAACAATGGGCGCTTTATGCAGATGGTTCAATACGGCCTCAGCAAAAC
4-GluLysAlaGluGlnGlnTrpAlaLeuTyrAlaAspGlySerIleArgProGlnGlnAsn
5-GluLysAlaGluGlnGlnTrpAlaLeuTyrAlaAspGlySerIleArgProGlnGlnAsn

CAAGATAACTGCCTTACAAGTGATGCTAATATACGAGAAACAATTGTCAAGACCCTCTCT
4-GlnAspAsnCysLeuThrSerAspAlaAsnIleArgGluThrIleValLysThrLeuSer
5-ArgAspAsnCysLeuThrSerAspSerAsnIleArgGluThrValValLysIleLeuSer

TGCAGCACTGCATCCTCCGGCCAGCGATGGATGTTCAAGAATGATGGAACCATTTGGAAT
4-CysSerThrAlaSerSerGlyGlnArgTrpMetPheLysAsnAspGlyThrIleTrpAsn
5-CysGlyProAlaSerSerGlyGlnArgTrpMetPheLysAsnAspGlyThrIleLeuAsn

TTGTATAATGGATTGGTGTTAGATGTGAAGCGATCGGATCCGACCCTTAAACAAATCATT
4-LeuTyrAsnGlyLeuValLeuAspValLysArgSerAspProThrLeuLysGlnIleIle
5-LeuTyrSerGlyLeuValLeuAspValArgAlaSerAspProSerLeuLysGlnIleIle

ATTTACCCTTTCCATGGAAACCCAAACCAAATATGGTTTCCACTATTTTGATAGACTAAT
4-IleTyrProPheHisGlyAsnProAsnGlnIleTrpPheProLeuPhe
5-LeuTyrProLeuHisGlyAspProAsnGlnIleTrpLeuProLeuPhe

TACCCTCTTGCAGTGTATGTATGTCCTACCATGAACATAGTTGCTTAAATAAAAAGGACA

TTGTAAATTAAAAAAAAAAAAAAAAA

FIG. 5a Junction Region for the Construction of pRTB601

```
                                                 |------ pRTB-151 --->
Hind III |--------------- ricin-B ---------------------------------->
         MetAlaAspValCysMetAspProGluProIleValArgIleValGlyArgAsnGlyLeu...
GACCATGATAAGCTTATGGCTGATGTTTGTATGGATCC        GCGTATCGTAGGTCGAAATGGTCTA...
                    TACCTAGGACTCGGGTATCACGCATAGCATCC      ACCAGAT...
         (oligo 2)                    (oligo 1)
```

FIG. 5b Fusion of lacZ and Ricin-B in pRTB236

```
   <------ lacZ ----------|   |------- ricin-B ---------------->
       MetThrMetIleThrProArgIleValGlyArgAsnGlyLeuCysValAspValArgAsp...
...CAGGAAACAGCTATGACCATGATTACGCCGCGTATCGTAGGTCGAAATGGTCTATGTGTTGATGTTAGGGAT...
   (RBS)
```

FIG. 5c Junction Region in pRTB514

```
                                |----------- ricin-B ------------>
   <------ pDG141 --------|  |------------ pRTB601 -------------->
                          MetAlaAspValCysMetAspProGluProIleValArgIle...
...AGTTC

FIG. 8

Key 1 natural ricin-B
2 pUC8
3 pRTB5
4 pRTB151
5 pRTB221
6 pRTB236
7 pRTB514
8 pRTB704
9 pRTB907

RECOMBINANT RICIN TOXIN FRAGMENTS

CROSS-REFERENCE TO RELATED APPLICATION

This is a continuation of U.S. application Ser. No. 06/717,319, filed Mar. 29, 1985, now abandoned, which is a continuation-in-part of U.S. application Ser. No. 06/578,121 filed Feb. 8, 1984, now abandoned.

DESCRIPTION

Technical Field

This invention relates to the production of toxin fragments using recombinant technology. More specifically, the invention relates to producing ricin toxin B fragment using recombinant means.

Background Art

Ricin toxin (RT or ricin) is a naturally occurring toxin composed of an enzymatically active, cytotoxic "A" amino acid sequence, and a "B" sequence, which is presumed to be responsible both for attaching the "A" sequence to a target cell to be killed, and to aid in the translocation of A fragment into the cytoplasm. Other examples of such toxins include diphtheria toxin and the exotoxin from *Pseudomonas aeruginosa*. Other toxic proteins, such as, for example, those derived from *Phytolacca americana* (PAPI, PAPII, and PAP-S) and gelonin show in vitro activities comparable to the "A" sequences of the above toxins, but are inactive in vivo, presumably due to the absence of a "B" chain.

The "ricin" peptides of the present invention are derived from the seeds of *Ricinus communis*, commonly known as castor beans. Two similar proteins (often called lectins) are extractable from these seeds: the above-mentioned ricin and *Ricin communis* agglutinin (RCA). Both proteins contain A and B portions; however, the A and B portions do not comprise a single peptide. The A portions of these moieties are capable of catalytically inactivating the large subunit of ribosomes in vitro and the mechanism of ricin for in vivo cytotoxicity is believed to reside in this capacity for ribosome inactivation. Ricin and RCA appear to be highly homologous (Cawley, D. B., et al, *Arch Biochem Biophys* (1978) 190:744) but differences exist. RCA is dramatically less toxic, and appears to exhibit characteristics corresponding to those expected of a dimer of ricin.

The components of ricin and of RCA have been well characterized and sequenced on the basis of the extracted materials (Funatsu, G., et al, *Agric Biol Chem* (1979) 43:2221). Ricin has an apparent molecular weight of 58,000 daltons and consists of the A chain with a molecular weight of 32,000 daltons and a B chain of molecular weight of 34,700 daltons. RCA is a tetramer which has two A subunits of molecular weight 32,000, and two B subunits of molecular weight 36,000 each. In their native environments, the B chains are generally glycosylated. The A and B subunits of both ricin and RCA are linked only by a single disulfide bond, and not by peptide linkage (Funatsu, G., et al, *Agri Biol Chem* (1977) 41:1211) unlike, for example diphtheria toxin which is found as a single chain peptide. It is also known that both ricin and RCA, though having separate peptides for A and B portions, are derived from a single chain precursor in each case (Butterworth, H. E., et al, *Eur J Biochem* (1983) 137:57). As a result of the work related to the present invention, it has been shown that the single chain precursor appears to contain a sequence of 12 amino acids between the A chain (amino terminal) and B chain sequence. It is assumed that upon excision of the dodecameric intervening peptide, the A and B chains remain linked through the single disulfide bond.

The present invention provides a means for obtaining the B chain of ricin using recombinant technology thus providing with greater accuracy the entire amino acid sequence, and making possible an exploration of the structural features required for its activity. The techniques and materials of the present invention further permit selective modification of the amino acid sequence of the B chain and thus permit manipulation to provide properties which are capable of enhancing the cytoxicity of ricin or of other toxins and the derivatives thereof. By enabling the production of ricin B chain using predictable, efficient, and economic procedures which, further, permit directed modification, the invention permits the use of B chain in practical and improved ways not before possible.

DISCLOSURE OF THE INVENTION

The invention relates, in one aspect, to ricin B which is prepared using recombinant techniques. The amino acid sequence of the ricin B can be, if desired, absolutely identical to the ricin B peptide amino acid sequence as extracted from castor bean seeds, but the recombinant product is inevitably somewhat modified due to the environment of its production, and may be further modified at the will of the producer to contain alterations in amino acid sequence or in the level of glycosylation. Accordingly, one aspect of the invention is a method of production of ricin B by recombinant techniques, and the ricin B so produced.

In other aspects, the invention is directed to expression vectors which are capable of effecting the expression of the ricin B chain, to host cells which have been transformed with such vectors, and to cultures thereof.

It has been possible to complete the preparation of the coding sequence for the ricin B protein using a novel sequence of reactions. A cloning vector containing a substantial portion of the ricin B encoding sequence was modified by digestion at a restriction site proximal to the 5' end of the cDNA insert in the cloning vector, followed by, as was necessary in this case, digestion with S1 nuclease sufficient to remove nucleotides intervening before the start of the cDNA insert, and treating with exonuclease III to provide 5' sticky ends. The sticky-ended vector was then treated with a mixture of two oligonucleotides, each of which contained a portion of the sequence required to complete the coding sequence for the N-terminus of the desired ricin B protein, and each of which had sufficient regions of overlap with respect to each other, and with respect to the 5' sticky ends of the cDNA sequence and of the cleaved vector sequence to form a tandem bridge of mostly single-stranded sequences. When made double-stranded by the action of DNA polymerase I large fragment (Klenow) and treated with ligase, these oligonucleotides and the exonuclease III treated vector generated the missing portions of the cDNA insert so as to provide the entire coding sequence for the desired protein, along with a convenient restriction site 5' of the start codon, and religated the vector.

This procedure offers a broadly applicable method to complete a desired DNA sequence or in general to modify, delete or add sequence to a double-stranded DNA to give a desired product DNA. It comprises digesting a vector DNA sequence with a restriction enzyme, removing any unwanted nucleotides, treating the cleaved vector with exonuclease III to create 5' sticky ends, mixing with the thus treated vector an even number of single-stranded nucleotides of alternating sense and anti-sense sequence which alternately encode or are complementary to the desired sequences in the product DNA, and which single-stranded oloqinucleotides have termini which overlap and are complementary to termini of the adjacent oligonucleotide(s) and/or cleaved vector 5' sticky ends so as to form a tandem bridge between the 5' sticky end upstream of the original cleavage site and the 5' sticky end downstream of the original cleavage site, and treating the mixture with DNA polymerase I (Klenow fragment) and ligase. This generalized procedure for modification of a double-stranded DNA sequence to give a desired product DNA sequence is also an aspect of the invention disclosed herein.

In still another aspect, the invention relates to improvements in the process for preparation of messenger RNAs which were applied to the process used in preparing the messenger encoding ricin B. One such improvement is specific for messenger RNA isolation from plant tissues, since plant extracts are accompanied by oxidized phenolics which are inhibitory to subsequent enzymatic manipulations such as, e.g., in vitro translation and reverse transcription. They can be removed by treating the preparation with Sephadex G-100. A further improvement, general to all mRNA preparations, comprises treating the preparation with a denaturant prior to the conventional dT affinity column separation of mRNA from ribosomal RNA.

BRIEF DESCRIPTION OF THE DRAWINGS

FIG. 1 is a diagramatic representation process for completing the coding sequence of an isolated cDNA using tandem single-stranded oligonucleotide bridges.

FIG. 2 shows the protein sequence of ricin B as disclosed by Funatsu (supra) and obtained from the extracted protein.

FIG. 3 shows the nucleotide sequence of the cDNA insert of the plasmid pRTB5 corresponding to the ricin B chain partial coding sequence, along with the amino acid sequence deduced from it. Also shown for comparison is the sequence of ricin B as determined from the extracted protein by Funatsu.

FIGS. 4*a* & 4*b* shows a comparison of base (4*a*) and protein (4*b*) sequence of the aforementioned cDNA insert with a cDNA insert of the plasmid pRTB4 which encodes a major portion of the sequence of the B portion of RCA. Also shown is the sequence of pRTA115, which overlaps a portion of the pRTB5 sequence.

FIG. 5*a* shows the sequences of the synthetic oligonucleotides used to complete the coding sequence of ricin B derived from pRTB5.

FIG. 5*b* shows the sequenced portion of pRTB236 representing the β-galactosidase/ricin B fusion.

FIG. 5*c* shows the sequenced portion of pRTB514 which contains the junction between the pDG141 ribosome binding site and the coding sequence from pRTB601.

FIG. 6 shows diagrammatically the construction of pRTB601.

FIG. 7 shows the construction of pRTB514, pRTB704, and pRTB907.

FIG. 8 shows a Western Blot of extracts from *E. coli* MM294 transformed with plasmids of the invention in comparison to ricin B.

MODES OF CARRYING OUT THE INVENTION

A. Definitions

As used herein, "ricin B" refers to a protein whose amino acid sequence is substantially similar to that of the ricin B peptide which is extractable from castor bean seeds. The ricin B of castor beans is approximately 260 amino acids in length and has a molecular weight of approximately 34,700 daltons. However, it is known that the precise sequence varies depending on the variety of bean.

"Substantially similar" means that the protein in question must be approximately the same length (arbitrarily within around 10%) but, more importantly, must retain the capacity of ricin B chain to facilitate the intracellularization of an associated toxin molecule. It is well known that some small alterations in protein sequence may be possible without disturbing the functional abilities of the protein molecule, although other modifications are totally destructive. It is not currently possible to predict with any assurance into which category a particular alteration will fall. The definition herein permits any modifications which are in the first category. Such alterations could result from chance mutations in the gene sequence or from deliberate alterations thereof. Further, as is well known, protein sequences may be modified by association with other molecules such as glycosides, lipids, or inorganic ions such as phosphate. The ionization status will also vary depending on the pH of the medium or the pH at which crystallization or precipitation of the isolated form occurs. Further, the presence of air may cause oxidation of labile groups, such as —SH. Intended within the definition of ricin B are all such modifications of a particular primary structure—ie, eg, both glycosylated and non-glycosylated forms, neutral forms, acid and basic salts, lipid or other associated peptide forms, side chain alterations due to oxidation or derivatization, and any other such modifications of an amino acid sequence which would be encoded by the same genetic codon sequence.

"Impurities" as used in describing ricin B prepared by the method of the invention refers to materials normally associated with ricin B as produced in the castor bean seeds, which are not included among the protein modifications above. Accordingly, "impurities" refers to ricin A and agglutinin as well as to other castor bean cellular materials which ordinarily are associated with ricin B non-specifically.

"Operably linked" when used in describing DNA sequences refers to juxtaposition in such a way that the functionality of the sequences is preserved. Thus, for example a coding sequence "operably linked" to a promoter is positioned so that the promoter is capable of effecting the expression of the coding sequence.

"Control" sequence refers to those DNA sequences which control initiation and termination of transcription and translation. In procaryotic systems, for example, control sequences comprise promoter or promoter/operator and nucleotides encoding a ribosome binding site.

"Recombinant host cells" refers to cells which have been transformed with DNA sequences constructed by recombinant techniques. Such reference includes both the cells as separated, for example by filtration or as a centrifugation pellet, and to cultures of these cells. Indeed, "cells" and "cell cultures," where the context so permits, are used interchangeably herein.

"Upstream cleavage terminus" and "downstream cleavage terminus" refer to the DNA sequence ends resulting when a double-stranded DNA is cleaved with a restriction enzyme. Depending on the enzyme used, the ends may be sticky or blunt. Using the usual convention, for the "upstream" terminus, the sense strand terminates with 3', and the anti-sense strand terminates with 5'; the opposite is true for the "downstream terminus".

"Comprised alternately of sense and anti-sense sequences" when used to describe a series of single-stranded oligonucleotides means that when arranged "approximately" end-to-end the oligonucleotides taken together will provide an entire sequence with each oligonucleotide sequence picking up in turn with sense-/anti-sense/sense/anti-sense, etc., ie, $$5'\text{———}\quad\text{———}\quad\text{———}\,\text{sense}$$
$$\text{———}\,5'\text{ anti-sense.}$$

By "approximately" in the foregoing paragraph is meant that the oligonucleotides may further overlap for no more than 89% of their length so that hybridization can occur at the termini, ie, $$5'\text{——}\overline{\text{III}}\underline{\text{III}}\quad\overline{\text{III}}\underline{\text{III}}\quad\overline{\text{III}}\underline{\text{III}}\quad\overline{\text{III}}\underline{\text{III}}\quad\overline{\text{III}}\text{ sense}$$
$$\text{———}\,5'\text{ anti-sense.}$$

"Contiguous with" when used to describe the relation of DNA sequences refers to a relationship such that one sequence is a continuation of the other, or complementary to a continuation of the other. However, the continuity may be "approximate" in the sense of the previous paragraph.

B. Cloning and Expression of the Ricin B Coding Sequence

The approach followed to obtain recombinant ricin B is, briefly, as follows:

1. The sequence published for naturally-occurring ricin B showed the presence of the amino acid sequence, Trp-Met-Phe-Lys-Asn-Asp-Gly (see FIG. 2), which is associated with minimal codon redundancy. A mixture of all oligonucleotide sequences encoding this sequence was constructed as a probe.

2. A cDNA library was constructed by isolating mRNA from castor bean seeds, and preparing the corresponding cDNA by, in general, conventional methods. However, during the construction, appropriate linkers were ligated to the ends of the cDNA so as to obtain inserts bounded by EcoRI/SalI sites. EcoRI/SalI inserts were then ligated into the cloning vector, pUC13, and transformed into *E. coli*. Successful transformants capable of hybridizing with the probe were selected and sequenced.

3. Colonies were obtained which contained large portions of the ricin B and agglutinin B sequences. In addition, a colony was obtained which contained the sequences for a portion of the putative peptide precursor of both RCA and ricin which was thus shown to contain a twelve amino acid bridging peptide. The cDNA insert contained a sequence which began in the A portion and overlapped into the B region of each. The plasmids derived from the foregoing colonies are designated pRTB5, pRTB4, and pRTA115, respectively, herein.

4. The cDNA insert in pRTB5, which contained the coding sequence for the entire ricin B chain except for the 11 N-terminal amino acids, was excised and placed in the correct orientation with respect to the lac promoter by insertion into pUC8, to give pRTB151. pRTB151 was modified by the procedure described in paragraph C below to add the appropriate coding sequences, a start codon, and a conveniently placed upstream HindIII site to give pRTB601. The cloning vector used to obtain the cDNA library contains a HindIII site immediately downstream of the SalI site used for ligation into the vector, and thus the entire coding sequence including the start codon can be excised by treatment of the modified vector with HindIII.

5. The coding sequence of the des-N-terminal ricin B in pRTB151 was placed into proper reading frame with the lac promoter to give pRTB236. Modest levels of expression could be obtained for the resultant fusion protein.

6. Improved expression was obtained by removing and religating the coding sequence as a HindIII cassette from pRTB601 to place it under the control of the trp promoter (pRTB514). Still further improvements in the level of expression could be obtained by utilizing a temperature-sensitive "$P_L$" promoter (pRTB704) and by employing a high copy number plasmid (pRTB907).

7. The protein produced by recombinant cells transformed with the resulting expression vectors pRTB236, pRTB514, pRTB704, and pRTB907 was shown to be the desired ricin B by Western Blot.

Details of the strategy described in this paragraph are set forth in paragraphs C–H below.

C. Gene Reconstruction by Tandem Bridging

In order to obtain the complete coding sequence for ricin B, including an additional start codon, a novel approach of general utility was employed. While devised to recreate the proper sequence for this particular protein, the techniques are applicable to any situation where cDNA library construction results in an incomplete copy of the coding sequence. They are also applicable even more generally to construction of a desired product double-stranded DNA sequence in a vector by modification of an available plasmid sequence.

The procedure is exemplified for specificity in terms of completing a missing sequence from the cDNA 5' terminus. It could, of course, be used to complete either or both termini, to insert a desired sequence into the middle of a gene or to perform a variety of other modification reactions.

Briefly, for example, the cloning vector containing the desired cDNA insert is digested at a restriction site immediately preceding the coding sequences obtained. There will, of course, be such a restriction site if the appropriate linkers have been used to insert the cDNA fragment in the first place. Extra bases intervening between this restriction site and the beginning of the coding sequence are removed, if present, by treating with S1 nuclease. The resulting digested vector, then, has upstream and downstream cleavage termini, the downstream terminus being the 5' end of the coding sequence and the upstream cleavage terminus being the sequences from the vector which were, before cleavage, immediately upstream of the cleavage site.

The two ends of the cleaved vector are then digested with exonuclease III. Exonuclease III hydrolizes nucleotide sequences which are in double-stranded status by digesting back beginning at the 3' terminus of each of the strands. Thus, treatment of the digested cloning vector with exonuclease III will result in an exposed 5' sticky end of the coding sequence at one end of the fragment and an exposed 5' sticky end of the vector ligated upstream of the cDNA sequence at the other. It is not critical how far back into the cDNA or vector fragment the sticky end must extend, but 100 bases or more of single-stranded fragment portion is workable. At least two single-stranded oligonucleotides, but in any event an even number, are then supplied. The first of these nucleotides is, for the most part, complementary to the codons which would immediately precede the 5' terminus of the cDNA codons, but also contains additional bases complementary to those in the exposed 5' terminus of the insert. The oligonucleotide supplied preferably should contain sufficient extension past the 5' terminus of the cDNA to pair with at least about 8 nucleotides.

The second oligonucleotide supplied should contain additional codons in the sense strand preceding those to which the first oligonucleotide is complementary. However, again, some area of overlap must be supplied to insure hybridization of the 3' terminus of the second oligonucleotide to the 3' terminus of the first. Additional single-stranded oligonucleotides may be supplied as necessary providing alternating additional complementary and coding sequences with overlapping regions.

The strategy is best understood diagrammatically as outlined in FIG. 1. As FIG. 1 shows, the cDNA is extended by a series of bridging oligonucleotides in tandem, with complementarity ensuring hybridization between corresponding termini, ie, 5' with 5' and 3' with 3', a final oligonucleotide linking the bridge with the cloning vector 5' sticky end.

The number of oligonucleotides required depends on the length of the sequence to be reconstructed. Each single-stranded oligonucleotide is more than about 18 bp in length and the regions of overlap at least about 8 bp at each terminus. The oligonucleotides are at least long enough so that when the overlap regions of complementarity are paired, at least 2 bases remain unpaired in the strand. If the reconstructed portion is, as in the illustration above, an N-terminus encoding sequence, an ATG start codon immediately preceding the codons of the desired sequence should be included and, optionally, for convenience, a restriction site preceding the ATG to permit easy manipulation of the resulting gene. If the codons to be replaced are at C-terminus, a stop codon should be included in appropriate reading frame, and can conveniently be followed by a convenient restriction site sequence.

The exonuclease III treated vector is then mixed with the appropriate oligonucleotides and the mixture treated with both DNA polymerase I (Klenow) to fill in the complementary strands and with *E. coli* or other ligase to complete the construction. The vector now contains the extended cDNA insert to include the entire sequence, preceded, if desired, by a restriction site.

It will be apparent from the foregoing description that this tandem bridging technique is useful for the insertion of any desired sequence into a circular vector. As nucleotides can also be removed adjacent the original cleavage site, the end result may be modification as well as insertion.

D. Improvements in mRNA Purification

In preparing the mRNA encoding ricin B, and its associated proteins, the method of Belamy, A. R., et al, *Methods in Enzymology* (1966) 104:156, was used with some modifications which effect improvements. These improvements and modifications overcome certain disadvantages of the standard methods. One such improvement succeeds in removing oxidized phenolic compounds from the preparations which constitute a problem in messenger RNA prepared from plant tissue sources. The other improvement has more general applicability in that it resolves a problem inherent in all mRNA preparation—ie, the tendency of mRNA to associate with ribosomal RNA. If this association can be destroyed before application of the preparation to the conventional dT affinity column, the requirements for elution are much less.

In order to eliminate oxidized phenolics, the preparation is treated with Sephadex G-100. The gel retains the oxidized phenolics and passes the mRNA in the void volume. (Both polyphenolic compounds and transfer RNA are retarded.) This offers a simpler solution than that conventionally used, ie, prior isolation of the ribosomes or other subcellular component before carrying out RNA extraction.

To eliminate the ribosomal RNA complexing, the procedure is modified so as to react the suspension of RNA emerging from the foregoing G-100 column, if such column is used, with a denaturant, or in any event so reacting it prior to applying the preparation to a dT affinity column. The preparation can be denatured with a minimal amount of a conventional denaturing agent such as, for example, heat, formamide, or methyl mercuric hydroxide, preferably formamide. The denaturing agent breaks down the association between the ribosomal RNA and polyA portions of the messenger RNA and thus permits the messenger to adhere to the column more effectively.

E. Vectors and Host Cells

The specific embodiments described hereinbelow set forth procedures for constructing vectors compatible with procaryotes, and for transformation of such vectors into these host cells. *E. coli* K12 strain, MM294 and a lambda lysogen of *E. coli* strain MC1000, are described in particular. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides markers which can be either retained or destroyed in constructing the desired vector. Commonly used procaryotic control sequences which are defined herein to include transcription initiation, optionally operator, and ribosome binding site sequences, include such commonly used promoters as the beta-lactamase (penicillinase) and lactose (lac) promoter systems (Chang, et al, *Nature* (1977) 198:1056) and the tryptophan (trp) promoter system (Goeddel, et al, *Nucleic Acids Res* (1980) 8:4057) and the lambda derived $P_L$ promoter and N-gene ribosome binding site (Shimatake, et al, *Nature* (1981) 292:128). However, any available promoter system compatible with procaryotes can be used.

In addition to bacteria, eucaryotic microbes, such as yeast, may also be used. *Saccharomyces cerevisiae*, Baker's yeast, is most commonly used although a number of other strains are commonly available. A number of plasmid vectors suitable for yeast expression are also known (see, for example, Stinchcomb, et al, *Nature* (1979) 282:39, and Tschempe, et al, *Gene* (1980) 10:157). Promoters for yeast vectors include promoters for the synthesis of glycolytic enzymes (Hess, et al, *J Adv Enzyme Reg* (1968)7:149; Holland, et al, *Biochemistry* (1978) 17:4900). Any vector containing a yeast compatible promoter, origin of replication and other control sequences is suitable.

More recently, it has been found possible to express genes encoding polypeptides in eucaryotic host cell cultures derived from multicellular organisms. See, for example, *Tissue Cultures,* Academic Press, Cruz and Patterson, editors (1973). Useful host cell lines include VERO and HeLa cells, and Chinese hamster ovary (CHO) cells. Expression vectors for such cells ordinarily include promoters compatible with mammalian cells such as, for example, the commonly used early and late promoters from Simian Virus 40 (SV 40) (Fiers, et al, *Nature* (1978) 273:113).

Depending on the host cell used, transformation is done using the calcium treatment employing calcium chloride, as described by Cohen, S. N., *Proc Natl Acad Sci (USA)* (1972) 69:2110, for procaryotes or other cells which contain substantial cell wall barriers, or, for mammalian cells without such cell walls, the calcium phosphate precipitation method of Graham and van der Eb, *Virology* ( 1978 ) 52:546.

The successful expression attained by the invention depends upon correct utilization of the suitable control sequences to regulate expression of the desired toxin fragment. Therefore, whatever the host, control sequences compatible with and suitable for that host are positioned in operably with respect to the coding sequence, using a properly placed "start" codon at the 5' end of the desired sequence. Any "native" control sequences are eliminated. The vectors of the invention place the coding sequence for the desired ricin B peptide fragments, immediately preceded by an ATG start codon directly downstream from control systems chosen to be compatible with the particular host.

It is also important, in obtaining good production of the desired fragments, to regulate the "time" of production so as to minimize any lethal effect on the host cell. Most typically, this is done by delaying expression of the ricin B sequences until substantial growth has occurred. Accordingly, it is desirable to utilize control sequences which are subject to environmental conditions. By maintaining conditions that repress expression during growth phase, and then converting to conditions which permit expression at the desired time, the negative aspects of any potentially lethal effect can be minimized.

In two particularly preferred approaches, these regulatable control sequences are compatible with procaryotic hosts. The trp promoter is a regulatable promoter where expression of the operably linked sequence can be controlled by the level of tryptophan in the medium. By maintaining high tryptophan levels during growth, expression is repressed. Depletion or competitive inhibition of tryptophan turns on the promoter and permits expression.

Still more preferred is the $P_L$ promoter derived from λ phage. This promoter is regulated by a protein which can be temperature sensitive. (There are mutant forms of the wild type repressor, eg, $CI_{857}$ which have this characteristic known in the art.) When used in a host which is able to synthesize this mutant form of repressor (such as *E. coli* K12 strain MC1000 lysogenic for the λ phage $N_7N_{53}CI_{857}SusP_{80}$), the $P_L$ promoter will be switched on when the temperature is raised because the higher temperature inactivates the mutant CI repressor. Thus, the host cells can be grown at low temperature without production of the foreign protein. The temperature is then raised when growth has been attained and ricin B production is desired.

Another, not necessarily independent approach, involves use of a plasmid which has temperature sensitive copy number control, so that if the cells are grown at low temperatures, coding sequences contained in the plasmid are replicated at low levels; at higher temperatures, the number of such copies is increased. The amount of protein produced is thus indirectly managed by regulating the number of available copies of its coding sequence.

If both approaches are used concomitantly, an increase in temperature results in both an increase in copy number and a derepression of promoter leading to substantial synthesis of otherwise repressed gene products.

F. Methods Employed

Isolation of the mRNA fragments comprising the desired coding sequences is described in detail herein below. The polyA RNA is used as a template to construct a cDNA library by means now well understood in the art. Details of such methods can be obtained by reference to Maniatis, E. F. et al, *Molecular Cloning,* Cold Spring Harbor Laboratory (1982). The cDNA library is probed for the desired sequences using the procedure of Grunstein and Hogness, *Proc Natl Acad Sci* (1975) 72:3961.

Vector construction employs ligation and restriction techniques known in the art. The quantity of DNA available can be increased by cloning the desired fragments, ie, inserting into a suitable cloning vehicle, such as pBR322, pUC13 or pUC8, transforming and replicating in *E. coli,* and, optionally further enhancing through chloramphenicol amplification or by phage replication. The desired fragments can then be removed from the cloning vectors or phage and ligated to suitable promoters compatible with the host intended to be employed in the expression of the gene. Such hosts are then transformed with these expression vectors and cultured under conditions which favor stabilization of the plasmid and the safe production of the desired toxin fragments. Such conditions might include repression of the controlling promoter until most of log phase growth has been completed, and then altering conditions so as to favor the synthesis of the peptide. When the peptide has been synthesized, the cells are lysed, and the desired fragment recovered from the lysate.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, eg, New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform followed by ether extraction and the nucleic acid is recovered from aqueous fractions by precipitation with ethanol followed by running over a Sephadex G-50 spin column. If desired, size separation of the cleaved fragments may be performed by polyacrylamide gel electrophoresis using standard techniques. A general description of size separations is Found in *Methods in Enzymology* (1980) 65:499–560.

Restriction cleaved fragments may be blunt ended by treating with the large fragment of *E. coli* DNA polymerase I (Klenow) in the presence of the four nucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 0.1 mM dNTPs. The Klenow fragment fills in at 5' sticky ends but chews back single strands, even though the four dNTPs are present, at 3' sticky ends. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column.

Two other nuclease enzymes are used in the procedures set forth below: S1 nuclease and exonuclease III.

Treatment with S1 nuclease under appropriate conditions results in rapid hydrolysis of any single-stranded portion of DNA and slow hydrolysis of double-stranded portions commencing at the ends. S1 nuclease hydrolyses are conducted in a buffer which is 15 mM sodium acetate, pH 4.5, 200 mM NaCl, and 1 mM $ZnSO_4$, using approximately 200 units per μl of S1 nuclease. Ordinarily, 5000 units of S1 nuclease is used to hydrolyze approximately 10 μg of DNA.

Exonuclease III attacks double-stranded DNA, but hydrolyzes beginning at the 3' end of the nucleotide sequence. Thus, digestion of a double-stranded DNA results in two 5' protruding sticky ends. Hydrolysis is carried out in a buffer containing 15 mM Tris, pH 8, 10 mM NaCl, 1 mM $MgCl_2$, and 0.1 mM DTT, using approximately 2000 units per µl exonuclease III. Ordinarily, 150 units of exonuclease III were used to react with 10 µg DNA.

Synthetic oligonucleotides are prepared by the triester method of Matteucci, et al (*J Am Chem Soc* (1981) 103:3185–3191). Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7 pmoles $\gamma^{32}$ P ATP (2.9 mCi/mmole), 0.1 mM spermidine, 0.1 mM EDTA.

Ligations are formed using approximately equimolar amounts of the desired DNA fragments (2–10×excess of linkers or small oligomers) suitably end tailored to provide correct matching, by treatment with an excess, i.e., in a typical 15–30 µl reaction 0.4–4 Weiss units T4 DNA ligase and, when blunt-ended ligation is involved, 0.4–1 units of RNA ligase. Ligation mixtures are buffered at approximately pH 7.6 using 66 mM Tris along with 5 mM magnesium ion, 5 mM dithiothreitol, 1 mM ATP, and 0.1 mg/ml BSA for either blunt-end or sticky end ligations. Incubations are carried out at approximately 14° to 25° C. overnight.

In vector construction employing "vector fragments," the vector fragment is sometimes treated with bacterial alkaline phosphatase (BAP) in order to remove the 5' phosphate and prevent religation of the vector. BAP digestions are conducted at pH 8.3 in approximately 50 mM Tris, in the presence of $Na^+$ and $Mg^{+2}$ using about 1 unit of BAP per µg of vector at 60° for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme cleavage of the unwanted fragments.

In the constructions set forth below, correct ligations for plasmid construction are confirmed by transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci* (1969) 62:1159, following chloramphenicol amplification (Clewell, D. B., *J Bacteriol* (1972) 110:667) and analyzed by restriction and/or sequenced by the method of Messing, et al, *Nucleic Acids Res* (1981) 9:309, or by the method of Maxam, et al, *Methods in Enzymology* (1980) 65:499.

Transformations in the examples below were performed using the calcium chloride method described by Cohen, S. N., et al, *Proc Natl Acad Sci* (USA) (1972) 69:2110.

Two host strains were used in cloning and expression of the plasmids set forth below:

For cloning and sequencing, in particular, *E. coli* strain MM294 (supra), Talmadge, K., et al, *Gene* (1980) 12:235; Meselson, M., et al, Nature (1968) 217:1110, was used as the host. However, when expression is under control of the $P_L$ promoter and $N_{RBS}$ the *E. coli* strain MC1000 Lambda $N_7N_{53}CI_{857}SusP_{80}$ as an expression host was used (ATCC 39531 deposited Dec. 21, 1983. This strain is hereinafter referred to as MC1000-39531.). This strain contains a lambda prophage which codes for a temperature sensitive $C_I$ repressor, which at the permissive temperature (30°–32° C.) is active. However, at the non-permissive temperature (36°–48° C.), the repressor is inactive and transcription from the $P_L$ promoter can proceed. It is further characteristic of this strain that at elevated temperatures the prophage fails to induce.

The following examples illustrate the invention by describing the production of expression vectors suitable for production of ricin B fragment in procaryotes. However, the ricin B of the invention can be ligated into a variety of vectors suitable for a range of other hosts.

G. Isolation of Messenger RNA and Preparation of a cDNA Library

G.1 Isolation of mRNA from Castor Beans 50 g castor beans (*Ricinus communis*) were placed in 100 ml homogenizing buffer (150 mM NaCl, 50 mM Tris, pH 8.3, 5 mM EDTA and 50 mM freshly added β-mercaptoethanol) to which was added 12 ml 0.2M vanadium-ribonucleoside complex,* 30 mg proteinase K, and 15 ml 20% SDS. The mixture was homogenized by blending at high speed for 3–4 min in a Waring blender and then incubating 2–3 hr at room temperature with occasional blending.

*The vanadium ribonucleoside solution is prepared as follows: 893 mg $VOSO_4.3H_2O$ was added to 2 ml water and the mixture boiled to dissolve the vanadium salt. A solution containing the 4 ribonucleosides was prepared by dissolving 1 mmole each of adenosine, cytidine, guanosine, and uridine in 17 ml water. Heat is required. 1 ml of the foregoing $VOSO_4$ solution was then added to the ribonucleoside solution and the resultant titrated to pH 6.5 with 10N NaOH, and finally to pH 7 with 1N NaOH while stirring in a boiling water bath. Formation of the complex is indicated by a change in color from bright blue to green-black. The solution was finally diluted to 20 ml with water.

The suspension was centrifuged for 15 min at 8000×g at 5° C. and the pellet discarded. The supernatant was strained through cheesecloth to remove lipids and the filtrate extracted sufficiently with Phenol:$CHCl_3$:isoamyl alcohol, 24:24:1 containing 1% hydroxy-quinoline, to remove vanadium salts and protein, and the aqueous layer brought to 0.4M with NaCl and 10 mM with EDTA. 2.5×volume absolute ethanol was added to precipitate nucleic acids, and the mixture stored at −20° C. overnight.

The precipitate was centrifuged for 15 min at 7000×g at 2° C., and the pellet resuspended in 9.5 ml aqueous solution 0.025M NaCl, 0.025M Tris, pH 8, plus 9.5 ml phosphate buffer (2.5M total phosphate, $K_2HPO_4$:33% $H_3PO_4$, 20:1), plus 9.5 ml 2-methoxyethanol. The mixture was shaken and chilled on ice for 3–5 min with occasional mixing, and then centrifuged at 2000×g for 5 min at 2° C. The upper layer was removed and to this was added 10 ml 0.2M sodium acetate, and 5 ml 1% cetyl trimethylammonium bromide (CTAB) and the mixture chilled on ice for 10 min. The resulting white precipitate was harvested by centrifugation at 2000×g for 10 min at 2° C. The precipitate was washed by addition of 70% ethanol in 0.1M sodium acetate and by re-centrifuging at 2500×g for 10 min at 4° C.

After removal of the supernatant, the pellet was resuspended in 2 ml G-100 column starting buffer (20 mM Tris, pH 8, 1 mM EDTA, 0.5% SDS), and then adjusted to contain 0.5M NaCl. Solids were removed by centrifugation at 2000×g for 5 min at room temperature and the supernatant applied to a Sephadex G-100 column (1.5 cm×40 cm) and the column eluted using buffer similar to that applied to the column but lacking SDS. The eluate was assayed by monitoring $OD_{260}$. Desired messenger RNA was obtained in the flow through volume, leaving behind oxidized phenolic compounds present in the plant extract. (These compounds are known to behave similarly to polyA RNA on dT columns, inhibit protein synthesis, and thus interfere with the assay for mRNA.)

The initial peak containing mRNA was treated with formamide, a denaturant, to destroy ribosomal RNA complexing. To do this, the mRNA containing fractions were pooled, precipitated in ethanol, and the precipitates redissolved in a minimum volume of water. To this solution was added 9 volumes of deionized formamide containing 20 mM PIPES (piperazine-N,N-bis(2-ethanesulfonic acid), pH 6.5–7.0.

The mixture was then warmed to 37° C. for 5 min, and 10 volumes of dT column buffer (0.5M NaCl, 10 mM Tris, pH 7.5, 1 mM EDTA) added. The presence of formamide dissociates the polyA RNA from any ribosomal RNA present.

The denatured mixture was then run over an oligo dT column according to procedures well established in the art, and approximately 100 μg polyA RNA recovered upon elution.

G.2 Formation of a cDNA Library

The polyA mRNA prepared as in the preceding paragraph was used to obtain a cDNA library according to the method of Maniatis, et al (supra). Briefly, a portion of the polyA RNA is treated under appropriate buffer conditions with reverse transcriptase and then treated with base to destroy the remaining mRNA. The resulting single-stranded cDNA is repaired using *E. coli* Polymerase I (Klenow fragment) in the presence of the 4 dNTPs and the resulting "hairpin" then ligated using T4 ligase to a SalI linker (obtained from New England BioLabs). After treating with S1 nuclease and repairing with Klenow, the blunt end was ligated to an EcoRI linker using $T_4$ ligase. After then digesting with EcoRI and SalI, the resulting double-stranded cDNA fragments, which are bounded by EcoRI and SalI restriction sites, were ligated into a EcoRI/SalI digested, BAP treated preparation of pUC13 obtained and freely available from J. Messing, the University of Minnesota. pUC13 is a modification of pBR322 capable of confering Amp resistance ($AmP^R$), which contains linkers bearing convenient restriction sites, including a PstI site downstream from the SalI site used in the insertion. The resulting ligation mixture was used to transform *E. coli* MM294, and $Amp^R$ strains selected.

Successful colonies were transferred onto nitrocellulose plates, and probed using the procedure of Grunstein & Hogness (supra), with the mixture of 16 synthetic oligonucleotides

$$5'\ CC\binom{A}{G}TC\binom{A}{G}TT\binom{C}{T}TT\binom{A}{G}AACATCC\ 3'$$

which is kinased with $^{32}P$. This mixture represents the anti-sense strand complementary to the codons for the amino acid sequence Trp-Met-Phe-Lys-Asn-Asp-Gly. Of about 5000 colonies probed about 1% were found which hybridized to the probe. Plasmids were isolated from several representations of these colonies, and analyzed by restriction analysis and Maxam-Gilbert sequencing. Three plasmids, pRTB4, pRTB5, and pRTA115 were sequenced in the insert region.

FIGS. 3 and 4 show the results of this sequencing. FIG. 3 shows the sequence of the insert in pRTB5. Line 1 in FIG. 3 represents the amino acid sequence of ricin B as determined by Funatsu (supra). The second line represents the amino acid sequence deduced from the pRTB5 base sequence. An examination of the deduced sequence shows a high level of correspondence, although some discrepancies exist. These are due to errors in the published sequence and to varietal differences in the ricin B proteins represented. Line 3 is the base sequence of the isolated cDNA. The entire coding sequence for ricin B is present except for codons for the first 11 amino acids. (The lower case codons at the 5' end represent the EcoRI linker used to ligate the cDNA insert into the plasmid.) pRTB5 was used as the source of the bulk of the coding sequence in the expression vectors.

FIG. 4 shows a comparison of the sequences in pRTB4 and pRTB5. It is believed that the pRTB4 sequence represents the coding for RCA B chain. FIG. 4 also shows the overlap between pRTA115 and pRTB5 which indicates that the RTA115 insert contains the upstream coding regions of the ricin B gene. Although pRTA115 is believed associated with the RCA precursor protein, the amino acid sequence deduced from pRTA115 for RCA matches that of ricin B for the 11 amino acids needed to complete the N-terminus. These sequences were therefore used as models for the construction of oligonucleotides encoding the missing 11 N-terminus codons and also permit the deduction of the amino acid sequence of the 12 amino acid peptide in the single peptide precursor of RCA and, presumably, of ricin A and B.

The coding sequences of pRTB5 were disposed so as not to be expressible under the control of the lac promoter as inserted into pUC13. Therefore, pRTB5 was cut with EcoRI and PstI and the vector cleaved into several fragments with BstNI. The insert fragment was ligated under standard conditions using T4 ligase with an EcoRI/PstI digest of pUC8, another modified pBR322 vector obtained from and freely available from Messing, J., at the University of Minnesota. pUC8 has EcoRI and PstI sites which place an EcoRI/PstI insert under lac promoter control as a fusion protein with the initial 5–8 amino acids of β-galactosidase. It also contains a HindIII site immediately downstream from the PstI site. The ligation mixture was transformed into *E. coli* MM294, and transformants selected for ampicillin resistance. Plasmid DNA was isolated from successful transformants in several colonies, and analyzed by restriction site mapping. Colonies showing the appropriate restriction patterns were selected. One colony, designated pRTB151, was tested for expression of the gene for the fusion protein. On Western Blot no protein band corresponding to the desired molecular weight was found, although cross-reacting proteins were produced. It was assumed that the reading frame might be improper, since this plasmid was designed to have the β-galactosidase and ricin B sequences in different phases.

H. Construction of the Ricin B Coding Sequence as a HindIII-Cassette—pRTB601

The construction is outlined in FIG. 6.

Ten μg of pRTB151 DNA was digested to completion with EcoRI, dissolved in 60 μl S1 buffer and digested for 4 min at room temperature under conditions which remove about 1 base pair of duplex DNA per min. DNA recovered from the foregoing buffer was dissolved in 60 μl exonuclease III buffer and digested for 4 min at room temperature. Subsequent analysis showed that the plasmid DNA had lost approximately 120 bp from each 3' end, leaving 5' ends available for hybridization. DNA recovered from the Exonuclease III buffer was dissolved in 50 μl water and 20 μl used in the ligation/repair reaction below.

Thus, 20 μl sample (2 pmoles) was mixed with 20 pmoles each of the synthetic oligonucleotides:

Oligo 2
5'- GACCATGATAAGCTTATGGCTGATGTTTGTATGGATCC and
      HindIII           3' TACCTAGGACTCGGGTATCACGCATAGCATCC-5'
                        Oligo 1 which have complementary sequences as shown, and wherein Oligo-2 encodes a HindIII site upstream of an ATG start codon as shown in FIG. 5a. The 5' end of Oligo-1 is complementary to 15 bases at the 5' end of the pRTB151 cDNA sequence as there shown and is complementary to the contiguous missing codons of the ricin B sequence. The 5' end of Oligo-2 is complementary to the 5' sticky end of the vector residue of the exonuclease III treated pRTB151.

The mixture was heated to 60° C. for 5 min in order to denature completely complementation of single-stranded DNA, cooled to 37° C. for 5 min to hybridized complementary strands, and then chilled on ice. The soluton was brought to polymerase I (Klenow) buffer conditions and reacted for 2 hr at 12° C. in the presence of the 50 μM each of the 4 dNTPs, 0.1 mM NAD, 0.3 units/μl Klenow, and 0.08 units/μl *E. coli* DNA ligase. The ligation mixture was used directly to transform competent *E. coli* MM294 and several thousand Amp® colonies found. Several hundred of these were replicated and grown on nitrocellulose filters and subjected to standard colony hybridization using $P^{32}$ kinased Oligo-2 as probe. Two clones which hybridized with the probe were analyzed by restriction analysis and sequenced, and a correct construction designated pRTB601. pRTB601 thus contains the ricin B coding sequence as a HindIII cassette. The upstream HindIII site is introduced immediately upstream of the ATG codon in Oligo-2; the downstream HindIII site arises from the pUC8 vector plasmid.

I. Construction of Expression Vectors for Ricin B

I.1 Construction of pRTB236 pRTB236 places the codons of pRTB5 under the control of lac Z promoter in proper reading frame so as to produce a fusion protein containing the initial 5 residues of β-galactosidase at the amino terminus followed by the peptide encoded by the cDNA insert in pRTB151. Thus, the resulting protein is a sequence begun with the β-galactosidase N-terminus and completed with the portion of ricin B lacking the first 11 amino acids.

To construct pRTB236, pRTB151 was modified to the correct reading frame as follows: pRTB151 was digested with EcoRI and treated with S1 nuclease to remove the EcoRI protruding ends. The reaction mixture was then religated using T4 DNA ligase, and transformed into *E. coli* MM294. $Amp^R$ colonies were selected, and a number of colonies sequenced. pRTB236 was found to be in the correct reading frame (the determined relevant sequence is shown in FIG. *6b*), and this transformed strain was capable of producing ricin B protein as shown by Western Blot.

FIG. 8 shows the results of Western Blot performed according to the procedure of Erlich, H. A., et al (*Infect Immunol* (1983) 41:683) on extracts from cells transformed with pRTB236, pRTB151, and pUC8. While cross-reacting material is seen in all clones containing the RTB sequence, only the extract from pRTB236 has a polypeptide of the proper size.

The construction of the plasmids pRTB514, pRTB704 and pRTB907 as described in paragraphs 1.2–I.4 is shown in FIG. 7.

I.2 Construction of pRTB514 pRTB514 contains the entire coding sequence of ricin B chain preceded by an ATG start codon under control of the trp promoter/operator system. The trp promoter operator system is derived from plasmid pDG141 which is further described below.

Three μg of pRTB601 was digested with HindIII to excise the ricin B coding sequence. The restriction digest was treated with FnuDII to destroy the $Amp^R$ region of the vector remainder, and ligated using T4 DNA ligase with a HindIII digest of 1 μg pDG141. The ligation mixture was transformed into *E. coli* MM294, and Amp® colonies selected. The desired plasmid pRTB514 was isolated from one colony and the correct construction confirmed by Maxam-Gilbert sequencing. The relevant sequence is shown in FIG. 5c.

I.2.a Preparation of pDG141 pDG141 contains the trp control sequences immediately upstream from an ATG start codon. It was deposited with the ATCC on 24 Jan. 1984, and given the accession number 39588. The sequence upstream of the ATG provides a HindIII cleavage site which cuts immediately downstream of a ribosome binding site. In the construction of pDG141, a derivative of pBR322 is used to provide a trp (PstI/HindIII) cassette and pBW20 to provide the ATG and a downstream SacI site.

Twelve μg of pBR322-Trp3 restricted with PstI and HindIII was ligated with 1.34 μg of similarly restricted pBW20. The ligation mixture was subsequently digested with BamHI to linearize any ligation products which contained the HindIII/PstI unwanted vector fragment from pBR322-Trp3. The ligation mixture was used to transform *E. coli* MM294, and the desired colonies selected on plates of L-Broth containing 50 μg/ml ampicillin pre-spread with 500 μg tryptophan. Correct construction was confirmed by sequencing.

I.2.a.1 Preparation of pBR322-trp3

The trp promoter/operator/ribosome binding site sequence, lacking the attenuator region, was obtained from pVH153, obtained from C. Yanofsky, Stanford University. Trp sequences are available in a variety of such plasmids known in the art. pVH153 was treated with HhaI (which cuts leaving an exposed 3' sticky end just 5' of the trp promoter) blunt-ended with Klenow, and partially digested with TaqI. The 99 bp fragment corresponding to restriction at the TaqI site, 6 nucleotides preceding the ATG start codon of trp leader was isolated, and then ligated to EcoRI(repair)/ClaI digested, pBR322 to provide pBR322-Trp 3. The aforementioned TaqI site encodes a 5' half ClaI site, hence ligation to a 3' half ClaI site (from pBR322) will regenerate a functional ClaI site. Additionally, the HindIII site immediately downstream from the pBR322 Cla site permits excision of the desired trp fragment as an EcoRI/HindIII cassette. pBR322-Trp3 was deposited with ATCC as pTRP3 and has accession no. 39946.

I.2.a.2 Construction of pBW20 pBW20 contains a synthetic ATG-containing dodecamer cloned into the HindIII/PvuII vector fragment from pBR322. The dodecamer, TATGAGCTCATA, contains SstI (or SacI) sites.

pBR322 was digested with HindIII, repaired with Klenow and the four dNTPs, and then digested with PvuII. The vector fragment was ligated with the self-complementary dodecamer and transformed into *E. coli* MM294 and the correct construction confirmed by plasmid isolation and sequencing.

I.3 Construction of pRTB704 pRTB704 is analogous to pRTB514 except that the coding sequence is under the control of the $P_L$-$N_{RBS}$ cassette. The construction is identical to that set forth in paragraph I.2 for pRTB514 except that pFC5 rather than pDG141 is used as a source of the HindIII digested plasmid which provides the promoter/operator and ribosome binding site encoding sequences. pRTB704 was deposited at ATCC on 14 Sep. 1984 and has accession no. 39865.

Alternatively, rather than pFC5, $pP_L322$ or $pP_L$Kan can also be used. The construction of these promoter providing plasmids is described as follows:

For each of these plasmids, the DNA sequence containing $P_L$ λ phage promoter and the ribosome binding site for the N-gene ($N_{RBS}$) is obtained from a derivative of pKC30 described by Shimatake and Rosenberg, *Nature* (1981) 292:128. pKC30 contains a 2.34 kb fragment from λ phage cloned into the HindIII/BamHI vector fragment from pBR322. The $P_L$ promoter and $N_{RBS}$ occupy a segment in pKC30 between a BglII and HpaI site. The derivative of pKC30 has the BglII site converted to an EcoRI site.

The BglII site immediately preceding the $P_L$ promoter was converted into an EcoRI site as follows: pKC30 was digested with BglII, repaired with Klenow and dNTPs and ligated with T4 ligase to an EcoRI linker (available from New England Biolabs) and transformed into *E. coli* K12 strain MM294 Lambda$^+$. Plasmids were isolated from Amp$^R$ Tet$^S$ transformants and the desired sequence confirmed by restriction analysis and sequencing. The resulting plasmid, pFC3, was double-digested with PvuI and HpaI to obtain an approximately 540 bp fragment framing the desired sequence. This fragment was partially digested with HinfI and the 424 bp fragment isolated and treated with Klenow and dATP, followed by S1 nuclease, to generate a blunt-ended fragment with the 3° terminal sequence —AG-GAGAA, where the —AGGAGA portion is the $N_{RBS}$. This fragment was restricted with EcoR1 to give a 347 base pair DNA fragment with 5'-EcoRI (sticky) and HinfI(partial repair S1 blunt)-3' termini.

I.3.a Preparation of pFC5 pβI-Z15, deposited 13 Jan. 1984, ATCC No. 39578, was prepared by fusing a sequence containing ATG plus 140 bp of β-IFN fused to lac Z into pBR322. In pβI-Z15, the EcoRI site of pBR322 is retained, and the insert contains a HindIII site immediately preceding the ATG start codon of β-IFN. pβ1-Z15 was restricted with HindIII, repaired with Klenow and dNTPs, and then digested with EcoRI. The resulting EcoRI/HindIII (repaired) vector fragment was ligated with the EcoRI/HinfI (repaired) fragment above, and the ligation mixture used to transform MC1000-39531. Transformants containing the successful construction were identified by ability to grow on lactose minimal plates at 34° C. but not at 30° C. (Transformations were plated on X-gal-Amp plates at 30° C. and 34° C. and minimal-lactose plates at 30° C. and 34° C. Transformants with the proper construction are blue on X-gal-Amp plates at both temperatures, but on minimal lactose plates, grow only at 34° C.) The successful construct was designated pFC5; pFC5 was deposited at ATCC on 14 Sep. 1984 and has accession no. 39864.

I.3.b Preparation of $pP_L322$

In the alternative, pBR322 may also be used as the cloning vector to carry the desired EcoRI/HindIII $P_L$-$N_{RBS}$ cassette. pBR322 was digested with HindIII, repaired with Klenow and dNTPs, and then further digested with EcoRI. The vector fragment was then ligated to the EcoRI/HinfI(repaired) fragment prepared above, and the ligation mixture transformed into MC1000-39531. Successful transformants were identified as Amp$^R$ Tet$^S$ colonies. Plasmids were isolated from successful transformants and a successful ligation was confirmed by sequencing, and designated $pP_L322$.

I.3.c Preparation of $pP_L$Kan

The third host plasmid vector used to obtain the cassette was pDG144, deposited 13 Jan. 1984, ATCC No. 39579. pDG144 is extensively described in another application and is not part of this invention. It is an altered pBR322 containing an intact Amp$^R$ gene, and a coding sequence for a protein capable of conferring resistance to kanamycin (Kan$^R$). The Kan$^R$ coding sequence is preceded by a synthetic polylinker. Since pDG144 contains neither a promoter nor a ribosome binding site preceding the coding sequence, Kan$^R$ is not expressed, and cells harboring pDG144 are sensitive to kanamycin and to structurally similar antibiotics. The polylinker sequence immediately preceding the ATG start codon for the kanamycin gene can be removed by digesting with EcoRI and HindIII and $P_L N_{RBS}$ inserted.

Accordingly, pDG144 was digested with HindIII, blunt-ended with Klenow and dNTPs, and then digested with EcoRI. The vector fragment was ligated with the above-prepared EcoRI/HinfI(repaired) fragment and transformed into MC1000-39531. Amp$^R$ Kan$^R$ colonies were selected, plasmids isolated and the correct sequence construction verified by restriction analysis and sequencing. One plasmid containing the correct sequence was designated $pP_L$Kan.

I.4 Construction of pRTB907 pRTB907 is analogous to pRTB704 except that the plasmid vector is a temperature sensitive high copy number plasmid. pRTB907 is derived from pRTB704 by excising the control and the coding sequences as an EcoRI/SalI digest, cleaving the pRTB704 vector portion with HhaI, and ligating this segment into EcoRI/SalI digested pCS3 described below. The ligation mixture was then used to transform MC1000-39531 and transformants selected by Amp$^R$. The correct construction of the desired plasmid was confirmed by restriction analysis.

I.4.a Construction of pCS3—A High Copy Number Plasmid pCS3 provides the origin of replication to insure high copy number for all of the foregoing dT expression vectors. The construction is described extensively in U.S. Ser. No. 541,948, filed Oct. 14, 1983, and now pending. This plasmid was deposited with the ATCC on Jun. 3, 1982, and given ATCC No. 39142.

pCS3 is derived from pEW27 and pOP9. pEW27 is described by E. M. Wong, *Proc Natl Acad Sci* (USA) (1982) 79:3570. It contains mutations near its origin of replication which provide for temperature regulation of copy number. As a result of these mutations replication occurs in high copy number at high temperatures, but at low copy number at lower temperatures.

pOP9 is a high copy number plasmid at all temperatures which was constructed by inserting into pBR322 the EcoRI/PvuII origin containing fragment from Col E1 type plasmid pOP6 (Gelfand, D., et al, *Proc Natl Acad Sci* (USA) (1978) 75:5869). Before insertion, this fragment was modified as follows: 50 μg of pOP6 was digested to completion with 20 units each BamHI and SstI. In order to eliminate the SstI 3' protruding ends and "fill in" the BamHI 5' ends, the digested pOP6 DNA was treated with *E. coli* DNA polymerase I (Klenow in a two-stage reaction first at 20° C. for elimination of the 3' SstI protruding end and then at 9° C. for repair at the 5' end. The blunt-ended fragment was digested and 0.02 pmole used to transform competent DG75 (O'Farrell, P., et al, *J Bacteriology* (1978) 134:645–654). Transformants were selected on L plates containing 50 μg/ml ampicillin and screened for a 3.3 kb deletion, loss of an SstI site, and presence of a newly formed BamHI site.

One candidate, designated pOP7, was chosen and the BamHI site deleted by digesting 25 μg of pOP7 with 20 units BamHI, repairing with *E. coli* DNA polymerase I fragment (Klenow), and religating with T4 DNA ligase. Competent DG75 was treated with 0.1 μg of the DNA and transformants selected on L plates containing 50 μg/ml ampicillin. Candidates were screened for the loss of the BamHI restriction site. pOP8 was selected. To obtain pOP9 the AvaI(repaired)/EcoRI $Tet^R$ fragment from pBR322 was prepared and isolated and ligated to the isolated PvuII(partial)/EcoRI 3560 bp fragment from pOP8.

Ligation of 1.42 kb EcoRI/AvaI(repair) $Tet^R$ (fragment A) and 3.56 kb EcoRI/PvuII $Amp^R$ (fragment B) used 0.5 μg of fragment B and 4.5 μg of fragment A in a two-stage reaction in order to favor intermolecular ligation of the EcoRI ends.

Competent DG75 was transformed with 5 μl of the ligation mixture, and transformants were selected on ampicillin (50 μg/ml) containing plates. pOP9, isolated from $Amp^R$ $Tet^R$ transformants showed high copy number, colicin resistance, single restriction sites for EcoRI, BamHI, PvuII, HindIII, 2 restriction sites for HincII, and the appropriate size and HaeIII digestion pattern.

To obtain pCS3, 50 μg pEW27 DNA was digested to completion with PvuII and then EcoRI. Similarly, 50 μg of pOP9 was digested to completion with PvuII and EcoRI and the 3.3 kb fragment was isolated.

0.36 μg (0.327 pmoles) pEW27 fragment and 0.35 μg (0.16 pmoles) pOP9 fragment were ligated and used to transform *E. coli* MM294. $Amp^R Tet^R$ transformants were selected. Successful colonies were initially screened at 30° C. and 41° C. on beta-lactamase assay plate and then for plasmid DNA levels following growth at 30° C. and 41° C. A successful candidate, designated pCS3, was confirmed by sequencing.

J. Production of Ricin B

*E. coli* MC1000-39531 transformed with either of the plasmids, pRTB704 and pRTB907, were grown at 30° C. in TYE' medium (15 g/l bactotryptone, 10 g/l yeast extract, 5 g/l NaCl supplemented with 1 mM $CaCl_2$) containing 100 μg/ml ampicillin. While in logarithmic growth phase, the temperature was increased to 42° C., and after 1.5 hr the cells were centrifuged and extracted with SDS. The extract was assayed by Western Blot as described above. The results are shown in FIG. 8, and contrasted with the results obtained with the analogous pRTB514 (using trp promoter) and with precursor and control plasmids. The lanes depicted are as follows: Lane 1, "native" ricin B, lanes 2–9, extracts of transformants with, respectively, pUC8, pRTB5, pRTB151, pRTB221 (a modified pRTB151), pRTB236, pRTB514, pRTB704, and pRTB907.

The materials listed below were deposited with the American Type Culture Collection, Rockville, Md., USA (ATCC). The deposits were made under the provisions of the Budapest Treaty on the International Recognition of the Deposit of Microorganisms for the Purposes of Patent Procedure and the Regulations thereunder (Budapest Treaty). Maintenance of a viable culture is assured for 30 years from date of deposit. The organism will be made available by ATCC under the terms of the Budapest Treaty, and subject to an agreement between Applicants and ATCC which assures unrestricted availability upon issuance of the pertinent US patent. Availability of the deposited strain is not be construed as a license to practice the invention in contravention of the rights granted under the authority of any government in accordance with its patent laws.

| Plasmid | Deposit Date | CMCC# | ATCC# |
|---|---|---|---|
| pDG144 | 13 Jan 1984 | — | 39579 |
| pFC5 | 15 Sept 1984 | 1935 | 39864 |
| pCS3 | 3 June 1982 | — | 39142 |
| pTRP3 | 18 Dec 1984 | 1731 | 39946 |
| pDG141 | 24 Jan 1984 | — | 39588 |
| pRTB704 | 14 Sept 1984 | 1951 | 39865 |
| pRAP229 | 8 March 1985 | 2218 | |
| *B. thuringiensis* | | 1615 | 39756 |

We claim:

1. A replicable, recombinant expression vector, comprising a DNA sequence encoding ricin B, wherein said expression vector is effective in expressing said DNA sequence encoding ricin B in recombinant host cells and wherein said expression vector is free of a DNA sequence encoding a cytotoxic ricin A chain.

2. Recombinant host cells transformed with the vector of claim 1.

3. A method of using the expression vector of claim 1 which comprises the steps of:

transforming a host cell with said expression vector, culturing said host cell transformed with said expression vector and recovering ricin B from the culture.

4. An expression vector comprising a DNA sequence encoding ricin B operably linked to transcriptional and translational control sequences compatible with a recombinant host cell, and free of a DNA sequence encoding a cytotoxic ricin A chain.

5. Recombinant host cells transformed with the vector of claim 4.

6. A method of using the expression vector of claim 4 which comprises the steps of:

transforming a host cell with said expression vector, culturing said host cell transformed with said expression vector and recovering ricin B from the culture.

7. An expression vector comprising a DNA sequence encoding ricin B, operably linked to bacterial transcriptional and translational control sequences compatible with a recombinant host cell of the genus Escherichia, and free of a DNA sequence encoding a cytotoxic ricin A chain.

8. A recombinant host cell of the genus Escherichia transformed with the vector of claim 7.

9. A method of using the expression vector of claim 7 which comprises the steps of transforming a host cell of the genus Escherichia with said expression vector, and culturing said transformed host cell, said transformed host cell expressing ricin B.

10. A DNA sequence encoding ricin B and free of a DNA sequence encoding a cytotoxic ricin A chain.

* * * * *